(12) United States Patent
Prakash

(10) Patent No.: US 7,193,103 B2
(45) Date of Patent: *Mar. 20, 2007

(54) SYNTHESIS OF N-[N-(3,3-DIMETHYLBUTYL)-L-α-ASPARTYL]-L-PHENYLALANINE 1-METHYL ESTER USING OXAZOLIDINONE DERIVATIVES

(75) Inventor: Indra Prakash, Hoffman Estates, IL (US)

(73) Assignee: The Nutrasweet Company, Chicago, IL (US)

( * ) Notice: Subject to any disclaimer, the term of this patent is extended or adjusted under 35 U.S.C. 154(b) by 269 days.

This patent is subject to a terminal disclaimer.

(21) Appl. No.: 10/902,143

(22) Filed: Jul. 30, 2004

(65) Prior Publication Data

US 2005/0014967 A1    Jan. 20, 2005

Related U.S. Application Data

(62) Division of application No. 09/859,439, filed on May 18, 2001, now Pat. No. 6,852,875.

(51) Int. Cl.
*C07C 229/00* (2006.01)
*C07D 263/42* (2006.01)

(52) U.S. Cl. .......................... 560/40; 560/41; 548/232

(58) Field of Classification Search ................ 560/40, 560/41; 548/232
See application file for complete search history.

(56) References Cited

U.S. PATENT DOCUMENTS

| 5,480,668 | A | 1/1996 | Nofre et al. | 426/548 |
| 5,510,508 | A | 4/1996 | Claude et al. | 560/41 |
| 5,728,862 | A | 3/1998 | Prakash | 560/40 |
| 6,077,962 | A | 6/2000 | Prakash et al. | 549/253 |
| 6,423,864 | B1 | 7/2002 | Prakash et al. | 560/41 |
| 6,852,875 | B2* | 2/2005 | Prakash | 560/40 |

FOREIGN PATENT DOCUMENTS

| CN | 1174844 | 3/1998 |
| WO | 00/15656 | 3/2000 |

OTHER PUBLICATIONS

Burger et al., "Regiospecific Reactions with Omega-Carboxy-Alpha-Amino Acids. A Simple Synthesis of Aspartame", Chemmiker Zeitlung 114(7-8), pp. 249-251 (1990).

* cited by examiner

*Primary Examiner*—Taylor Victor Oh
(74) *Attorney, Agent, or Firm*—Fitzpatrick, Cella, Harper & Scinto

(57) ABSTRACT

Synthesis of N-[N-(3,3-dimethylbutyl)-L-α-aspartyl]-L-phenylalanine 1-methyl ester by treating N-(3,3-dimethylbutyl)-L-aspartic acid with ketones to give oxazolidinone derivatives, which are condensed with L-phenylalanine methyl ester.

18 Claims, No Drawings

SYNTHESIS OF N-[N-(3,3-DIMETHYLBUTYL)-L-α-ASPARTYL]-L-PHENYLALANINE 1-METHYL ESTER USING OXAZOLIDINONE DERIVATIVES

This application is a division of application Ser. No. 09/859,439 filed May 18, 2001, now U.S. Pat. No. 6,852,875 which claims the benefit of U.S. Provisional Patent Application No. 60/205,694, filed May 19, 2000, the entire disclosure of each of which is incorporated herein by reference.

BACKGROUND OF THE INVENTION

1. Field of the Invention

This invention relates to the synthesis of N-[N-(3,3-dimethylbutyl)-L-α-aspartyl]-L-phenylalanine 1-methyl ester (neotame) using novel oxazolidinone derivatives. This method of producing neotame is an alternative to the conventional synthetic route for producing neotame which uses aspartame as a starting material.

2. Related Background Art

N-[N-(3,3-dimethylbutyl)-L-α-aspartyl]-L-phenylalanine 1-methyl ester (neotame) is a high potency dipeptide sweetener (about 8000× sweeter than sucrose) that has the formula

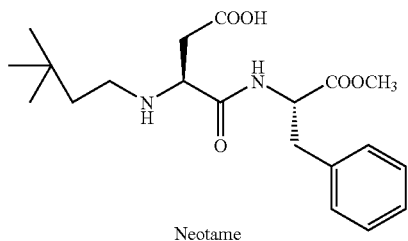

Neotame

Neotame may be synthesized using a variety of synthetic methods. The chemical synthesis of neotame is disclosed in U.S. Pat. No. 5,480,668, U.S. Pat. No. 5,510,508, U.S. Pat. No. 5,728,862, U.S. Pat. No. 6,077,962 and WO 00/15656, the disclosure of each of which is incorporated by reference herein.

U.S. Pat. Nos. 5,510,508 and 5,728,862 describe the synthesis of neotame by hydrogenation of a mixture of aspartame and 3,3-dimethylbutyraldehyde with a catalyst such as Pd on carbon. This synthesis is represented by the following equation.

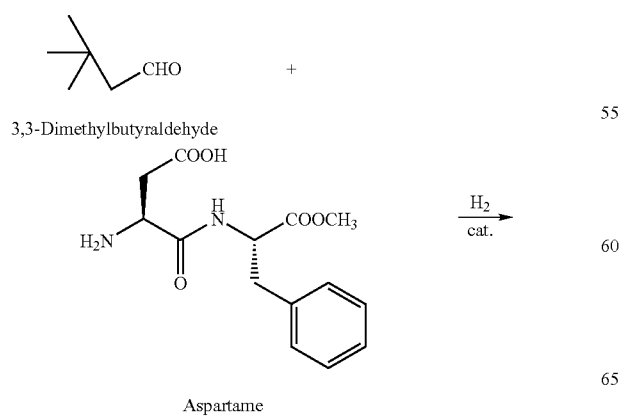

International Patent Publication No. WO 00/15656 describes the formation of neotame by hydrogenation of a mixture of 3,3-dimethylbutyraldehyde and Z-aspartame (N-benzyloxycarbonyl-L-α-aspartyl-L-phenylalanine-1-methyl ester) in a methanolic solvent. U.S. Pat. No. 6,077,962 describes the synthesis of neotame using a peptide coupling method of an activated derivative of N-(3,3-dimethylbutyl)-L-aspartic acid and L-phenylalanine or L-phenylalanine methyl ester.

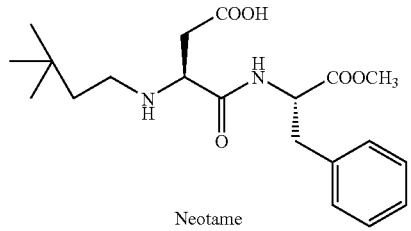

Neotame

The literature teaches regioselective methods for the formation of α-aspartyl peptide bonds, as opposed to β-aspartyl peptide bonds, in the synthesis of aspartame. One of these methods comprises the cyclocondensation of carbonyl compounds with N-protected aspartic acid as described in Chinese Patent CN 11748844 A. The resulting oxazolidinone derivative, having the structure

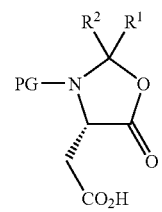

wherein PG is a protecting group, $R^1$ is H or $R^2$, $R^2$ is $CX_3$ and X is Cl, Br or F, has the α-aspartyl carbonyl as an ester and the β-aspartyl carbonyl as a carboxylic acid. Thus, only the α-aspartyl carbonyl is activated for peptide bond formation. The nitrogen protecting groups included Z, Boc, formyl and acetyl groups.

Other examples in the literature teach regioselective methods for the formation of α-aspartyl peptide bonds, as opposed to β-aspartyl peptide bonds. Such methods comprise the cyclocondensation of carbonyl compounds with aspartic acid without nitrogen protection. In these cases, the nitrogen of the oxazolidinone derivative having the structure

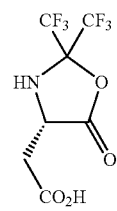

is an amine and not part of an amide, as was the case where nitrogen was protected.

The treatment of neohexyl-L-aspartic acid with carbonyl compounds to form oxazolidinone derivatives useful in the selective preparation of neotame without the formation of the beta isomer is not described in the above-described art.

It would be desirable, however, to develop more efficient and cost-effective methods of preparing high purity neotame from readily available or readily obtainable materials.

SUMMARY OF THE INVENTION

The present invention relates to the synthesis of N-[N-(3,3-dimethylbutyl)-L-α-aspartyl]-L-phenylalanine 1-methyl ester via novel oxazolidinone derivatives.

According to the present inventive method, neotame is synthesized by reacting N-(3,3-dimethylbutyl)-L-aspartic acid and a ketone in a solvent for a time and at a temperature sufficient to produce an oxazolidinone derivative and by reacting the oxazolidinone derivative and phenylalanine or phenylalanine methyl ester in the solvent for a time and at a temperature sufficient to produce N-[N-(3,3-dimethylbutyl)-L-α-aspartyl]-L-phenylalanine 1-methyl ester.

The present invention relates to the regioselective formation of N-alkylated α-aspartyl amides via the use of ketones, and particularly to the use of such regioselective processing to obtain oxazolidinone derivatives which can react with L-phenylalanine methyl ester in a solvent with or without acid and/or a catalyst to yield N-[N-(3,3-dimethylbutyl)-L-α-aspartyl]-L-phenylalanine 1-methyl ester (neotame) with the usual work-up. The present synthetic method is represented by the following reaction scheme:

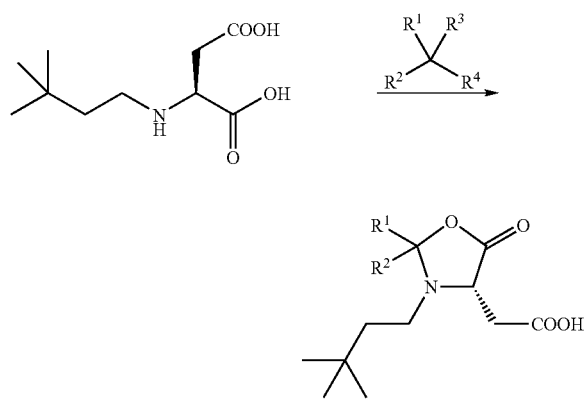

wherein $R^1$ is $R^2$, $R^2$ is Ph or $CX_3$, X is H, Cl, Br or F, $R^3$ and $R^4$ taken together is =O, or $R^3$, and $R^4$ are the same and are $OCH_3$ or $OC_2H_5$

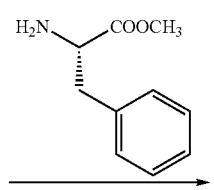

-continued

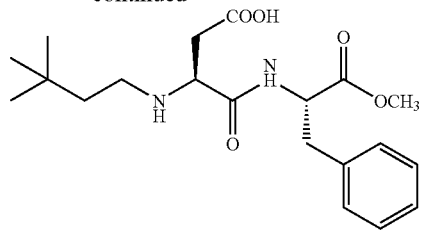

According to the present invention, neotame is synthesized by reacting N-(3,3-dimethylbutyl)-L-aspartic acid and a ketone in a first solvent for a time and at a temperature sufficient to produce an oxazolidinone derivative and by reacting the oxazolidinone derivative and phenylalanine or phenylalanine methyl ester in a second solvent for a time and at a temperature sufficient to produce N-[N-(3,3-dimethylbutyl)-L-α-aspartyl]-L-phenylalanine 1-methyl ester.

According to the first step of the present inventive method, an admixture of N-(3,3-dimethylbutyl)-L-aspartic acid and a ketone are reacted in a first solvent for a time and at a temperature sufficient to produce an oxazolidinone derivative.

Ketones of the formula $R^1R^2C=O$ or acetals of ketones of the formula $CR^1R^2R^3R^4$, wherein $R^1$ is $R^2$, $R^2$ is Ph or $CX_3$, X is H, Cl, Br or F, $R^3$ and $R^4$ taken together is =O, or $R^3$ and $R^4$ are the same and are $OCH_3$ or $OC_2H_5$ are suitable for use in the present invention. Ph is phenyl or substituted phenyl. Suitable ketones include, without limitation, hexafluoroacetone, 1,1,1-trifluoroacetone, hexachloroacetone, and combinations thereof.

N-(3,3-dimethylbutyl)-L-aspartic acid is prepared as described in U.S. Pat. No. 6,077,962, the disclosure of which is incorporated by reference herein. The ketones are readily available starting materials. The N-(3,3-dimethylbutyl)-L-aspartic acid and the ketone are typically combined in a molar ratio ranging from about 1:1 to about 1:4.

The solvents suitable for use as the first solvent in the present invention are limited only by reactivity considerations; in other words, the solvent must not react with the oxazolidinone derivative, the phenylalanine nucleophile or the resulting product, thereby impeding or prohibiting the desired reaction. Suitable solvents include, without limitation, tetrahydrofuran, diethyl ether, t-butyl methyl ether, ethyl acetate, dioxane, toluene, butyl acetate, methyl acetate, dichloromethane, dimethylformamide, dimethylsulfoxide and combinations thereof.

Generally, the time sufficient to produce an oxazolidinone derivative ranges from about 1 to about 48 hours, preferably from about 2 to about 24 hours. Generally, the temperature sufficient to produce neotame according to the present invention ranges from about 20° C. to about 150° C., preferably from about 22° C. to about 70° C.

In certain embodiments of the present invention, a catalyst may be present during the reaction of N-(3,3-dimethylbutyl)-L-aspartic acid and the ketone. Suitable catalysts include, without limitation, p-toluenesulfonic acid. In certain embodiments of the present invention, an acid may be present during the reaction of N-(3,3-dimethylbutyl)-L-aspartic acid and the ketone. Suitable acids include, without limitation, formic acid, p-toluenesulfonic acid, methane sulfonic acid, 10-camphorsulfonic acid and combinations thereof.

According to the second step of the present inventive method, an admixture of the oxazolidinone derivative and phenylalanine or L-phenylalanine methyl ester are reacted in a second solvent for a time and at a temperature sufficient to produce N-[N-(3,3-dimethylbutyl)-L-α-aspartyl]-L-phenylalanine 1-methyl ester.

L-phenylalanine methyl ester is a readily available starting material. Typically, the L-phenylalanine methyl ester is used in a molar ratio with the oxazolidinone derivative produced in the first step of the present invention ranging from about 1:1 to about 1:2.

Generally, the time sufficient to produce N-[N-(3,3-dimethylbutyl)-L-α-aspartyl]-L-phenylalanine 1-methyl ester ranges from about 1 to about 48 hours, preferably from about 12 to about 24 hours. Generally, the temperature sufficient to produce neotame according to the present invention ranges from about 0° C. to about 50° C., preferably from about 22° C. to about 40° C.

The solvents suitable for use as the second solvent in the present invention are limited only by reactivity considerations; in other words, the solvent must not react with the oxazolidinone derivative, the phenylalanine nucleophile or the resulting product, thereby impeding or prohibiting the desired reaction. Suitable solvents include, without limitation, tetrahydrofuran, diethyl ether, t-butyl methyl ether, ethyl acetate, dioxane, toluene, butyl acetate, methyl acetate, dichloromethane, dimethylformamide, dimethylsulfoxide and combinations thereof. In certain embodiments of the present invention, the first solvent and the second solvent used in the first and second steps, respectively, are the same solvent.

The present invention may also include additional steps. Such additional steps include, without limitation, solvent concentration adjustment, seeding, cooling (crystallization), and neotame isolation.

Typically crystallization of neotame is accomplished by cooling the mixture to about 0–25° C., preferably to about 5–10° C., over the course of about 0.5–2 hours, preferably about 1–2 hours.

Seeding prior to or during crystallization can initiate a controlled crystal growth rate according to the present invention. Hence, the reaction mixture may optionally be seeded in an amount from 0.0001%–10%, by weight of the N-[N-(3,3-dimethylbutyl)-L-α-aspartyl]-L-phenylalanine 1-methyl ester in the solution, preferably from 0.1% to 1% and most preferably from 0.1% to 0.5%. Seeding is typically performed at 25–35° C. and preferably at 28–30° C.

The reaction mixture may be unstirred or stirred while neotame crystallizes according to the present invention.

Crystallized neotame may be separated from the solvent solution by a variety of solid-liquid separation techniques that utilize centrifugal force, that include, without limitation, vertical and horizontal perforated basket centrifuge, solid bowl centrifuge, decanter centrifuge, peeler type centrifuge, pusher type centrifuge, Heinkel type centrifuge, disc stack centrifuge and cyclone separation. Additionally, separation may be enhanced by any of pressure, vacuum, and gravity filtration methods, that include, without limitation, the use of belt, drum, nutsche type, leaf, plate, Rosenmund type, sparkler type, and bag filters and filter press. Operation of the neotame solid-liquid separation device may be continuous, semi-continuous or in batch mode. The neotame solid may also be washed on the separation device using various liquid solvents, including, without limitation, water, methanol and mixtures thereof. The neotame solid can also be partially and totally dried on the separation device using any number of gases, including, without limitation, nitrogen and air, to evaporate residual liquid solvent. The neotame solid may be automatically or manually removed from the separation device using liquids, gases or mechanical means by either dissolving the solid or maintaining the solid form.

The neotame synthesized according to the present invention may be purified by any known method including, but not limited to, the following methods. U.S. Pat. No. 5,728,862 outlines a purification method by which neotame is precipitated out of an aqueous/organic solvent solution, wherein the aqueous/organic solvent solution has an amount of organic solvent of about 17% to about 30% by weight. Copending U.S. patent application Ser. No. 09/448,671, filed on Nov. 24, 1999, relates to methods of purifying neotame by crystallization in a variety of organic solvent/aqueous organic solvent mixtures; each of these methods involves the use of an organic solvent and water mixture and solvent distillation. Copending U.S. patent application Ser. No. 09/449,314, filed on Nov. 24, 1999, relates to methods of purifying neotame using chromatography.

The neotame synthesized according to the present invention is the monohydrate, which may be dried to produce an anhydrous form.

The crystallized and isolated neotame solid may be further purified by a variety of drying methods. Such methods are known to those skilled in the art and include, but are not limited to, the use of a rotary vacuum dryer, fluid bed dryer, rotary tunnel dryer, plate dryer, tray dryer, Nauta type dryer, spray dryer, flash dryer, micron dryer, pan dryer, high and low speed paddle dryer and microwave dryer.

The Examples which follow are intended as an illustration of certain preferred embodiments of the invention, and no limitation of the invention is implied.

EXAMPLE 1

4-Carbomethoxy-3-N-(3,3-dimethylbutyl)-2,2-bis (trifluoro-methyl)oxazolidin-5-one A gas flow of hexafluoroacetone is blown at a moderate rate at room temperature onto an intensely stirred suspension of 100 mmol of N-(3,3-dimethylbutyl)-L-aspartic acid in 40 ml anhydrous dimethylsulfoxide. The absorption of the gas starts after a short induction period. The gas flow is adjusted in a way that an excess of hexafluoroacetone is always present but that any condensation of hexafluoroacetone at a $CO_2$-radiator is avoided. The end of the reaction is recognized by the beginning backflow of hexafluoroacetone. A clear suspension is formed. After further stirring for 2–3 hours, the reaction solution will be decanted onto 200 ml of ice water and extracted three times with 100 ml ethyl acetate each time. In order to remove any remaining dimethylsulfoxide and hexafluoroacetone hydrate, the combined solutions of ethyl acetate are washed three times with 50 ml ice water and dried over anhydrous sodium sulfate. After removal of the solvent under reduced pressure, the compounds crystallize out.

EXAMPLE 2

N-[N-(3,3-dimethylbutyl)-L-α-aspartyl]-L-phenylalanine 1-methyl ester

To a solution of 20 mmol of 4-carbomethoxy-3-N-(3,3-dimethylbutyl)-2,2-bis(trifluoromethyl)oxazolidin-5-one in 50 ml anhydrous diethyl ether, a solution of 4.25 g (24 mmol) L-phenylalanine methyl ester in 5 ml anhydrous diethyl ether is added dropwise with stirring at room temperature. A crystalline solid substance begins to precipitate within a few minutes. The reaction finishes within 24 hours.

EXAMPLE 3

2-[(4S)-3-(3,3-dimethylbutyl)-5-oxo-2,2-bis(trifluoromethyl)-1,3-oxazolan-4-yl]acetic acid A gas flow of hexafluoroacetone is blown at a moderate rate at room temperature onto an intensely stirred suspension of 10 mmol of N-(3,3-dimethylbutyl)-L-aspartic acid in 20 ml 1,4-dioxane. A clear solution is formed overnight. The solvent was removed in vacuo, and the oily residue was confirmed to be an almost quantitative amount of 2-[(4S)-3-(3,3-dimethylbutyl)-5-oxo-2,2-bis(trifluoromethyl)-1,3-oxazolan-4-yl]acetic acid by NMR.

EXAMPLE 4

N-[N-(3,3-dimethylbutyl)-L-α-aspartyl]-L-phenylalanine 1-methyl ester

2-[(4S)-3-(3,3-dimethylbutyl)-5-oxo-2,2-bis(trifluoromethyl)-1,3-oxazolan-4-yl]acetic acid (2 mmol) and L-phenylalanine 1-methyl ester (2 mmol) were dissolved in tetrahydrofuran (15 ml). The mixture was stirred at room temperature for 24 hours. The solvent was removed in vacuo to yield an oil. A white solid, confirmed to be neotame by NMR, was obtained after stirring the oil in water overnight. Neotame was obtained in 90% yield.

EXAMPLE 5

N-[N-(3,3-dimethylbutyl)-L-α-aspartyl]-L-phenylalanine 1-methyl ester

L-phenylalanine 1-methyl ester hydrochloride (10 mmol), tetrahydrofuran (15 ml) and sodium acetate (NaOAc, 10 mmol) were loaded into a 50 ml flask. The mixture was stirred at room temperature for 15 minutes. A solution of 2-[(4S)-3-(3,3-dimethylbutyl)-5-oxo-2,2-bis(trifluoromethyl)-1,3-oxazolan-4-yl]acetic acid (10 mmol) in tetrahydrofuran (10 ml) was added to the mixture. The mixture was then stirred at room temperature for 24 hours. The solvent was removed in vacuo to yield a residue. The residue was stirred in water overnight at room temperature. The precipitated solid was filtered, washed with water and dried to yield neotame in 90% yield.

EXAMPLE 6

2-[(4S)-3-(3,3-dimethylbutyl)-5-oxo-2,2-bis(trifluoromethyl)-1,3-oxazolan-4-yl]acetic acid Neo-aspartic acid (5 mmol) was dissolved in 2,2-dimethoxypropane (10 ml) and 1,4-dioxane (10 ml). p-Toluenesulfonic acid (0.5 mmol) was added to the reaction mixture and refluxed for 48 hours. The solvent was removed from the reaction mixture, extraction using dichloromethane was performed, the organic layer was concentrated by vacuo and the residue was checked via 1H NMR. 2-[(4S)-3-(3,3-dimethylbutyl)-5-oxo-2,2-bis(trifluoromethyl)-1,3-oxazolan-4-yl]acetic acid was obtained in about a 20% yield and with low purity.

Other variations and modifications of this invention will be obvious to those skilled in this art. This invention is not to be limited except as set forth in the following claims.

What is claimed is:

1. A process of synthesizing N-[N-(3,3-dimethylbutyl)-L-α-aspartyl]-L-phenylalanine 1-methyl ester comprising the steps of:
   (a) reacting an admixture of (i) N-(3,3-dimethylbutyl)-L-aspartic acid and (ii) a ketone or an acetal of a ketone in a first solvent for a time and at a temperature sufficient to produce an oxazolidinone derivative having the formula

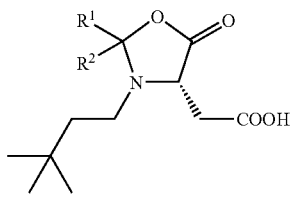

wherein $R^1$ is $R^2$; $R^2$ is Ph or $CX_3$; and X is H, Cl, Br or F; and
   (b) reacting an admixture of the oxazolidinone derivative and L-phenylalanine or L-phenylalanine methyl ester in a second solvent for a time and at a temperature sufficient to produce N-[N-(3,3-dimethylbutyl)-L-α-aspartyl]-L-phenylalanine 1-methyl ester,
   wherein the first solvent and the second solvent are different.

2. The process according to claim 1, wherein the ketone is selected from the group consisting of hexafluoroacetone, hexachloroacetone, and combinations thereof.

3. The process according to claim 1, wherein the acetal of a ketone is selected from the group consisting of dimethyl acetal of hexafluoroacetone, diethyl acetal of hexafluoroacetone, dimethyl acetal of hexachloroacetone, diethyl acetal of hexachloroacetone, and combinations thereof.

4. The process according to claim 1, wherein the first solvent is selected from the group consisting of tetrahydrofuran, diethyl ether, t-butyl methyl ether, ethyl acetate, dioxane, toluene, butyl acetate, methyl acetate, dichloromethane, dimethylformamide, dimethylsulfoxide and combinations thereof.

5. The process according to claim 1, wherein the ratio of N-(3,3-dimethylbutyl)-L-aspartic acid to the ketone or the acetal of a ketone is from about 1:1 to about 1:4.

6. The process according to claim 1, wherein the temperature sufficient to produce the oxazolidinone derivative is from about 20° C. to about 150° C.

7. The process according to claim 6, wherein the temperature sufficient to produce the oxazolidinone derivative is from about 22° C. to about 70° C.

8. The process according to claim 1, wherein the time sufficient to produce the oxazolidinone derivative is from about 1 hour to about 48 hours.

9. The process according to claim 8, wherein the time sufficient to produce the oxazolidinone derivative is from about 12 hours to about 24 hours.

10. The process according to claim 1, wherein the admixture of N-(3,3-dimethylbutyl)-L-aspartic acid and the ketone or the acetal of a ketone further comprises a p-toluenesulfonic acid catalyst.

11. The process according to claim 1, wherein the admixture of N-(3,3-dimethylbutyl)-L-aspartic acid and the ketone or the acetal of a ketone further comprises an acid.

12. The process according to claim 11, wherein the acid is selected from the group consisting of formic acid, acetic acid, p-toluenesulfonic acid, methane sulfonic acid and combinations thereof.

13. The process according to claim 1, wherein the second solvent is selected from the group consisting of tetrahydrofuran, diethyl ether, t-butyl methyl ether, ethyl acetate, dioxane, toluene, butyl acetate, methyl acetate, dichloromethane, dimethylformamide, dimethylsulfoxide and combinations thereof.

14. The process according to claim 1, wherein the ratio of L-phenylalanine or L-phenylalanine methyl ester to the oxazolidinone derivative is from about 1:1 to about 1:2.

15. The process according to claim 1, wherein the temperature sufficient to produce N-[N-(3,3-dimethylbutyl)-L-α-aspartyl]-L-phenylalanine 1-methyl ester is from about 0° C. to about 50° C.

16. The process according to claim 15, wherein the temperature sufficient to produce N-[N-(3,3-dimethylbutyl)-L-α-aspartyl]-L-phenylalanine 1-methyl ester is from about 22° C. to about 40° C.

17. The process according to claim 1, wherein the time sufficient to produce N-[N-(3,3-dimethylbutyl)-L-α-aspartyl]-L-phenylalanine 1-methyl ester is from about 1 hour to about 48 hours.

18. The process according to claim 17, wherein the time sufficient to produce N-[N-(3,3-dimethylbutyl)-L-α-aspartyl]-L-phenylalanine 1-methyl ester is from about 12 hours to about 24 hours.

* * * * *